United States Patent
James

(10) Patent No.: US 9,486,125 B2
(45) Date of Patent: Nov. 8, 2016

(54) ACCESSORY CLIP FOR AN ENDOSCOPE

(75) Inventor: Adam Graham James, London (GB)

(73) Assignee: Endoguard Limited (GB)

( * ) Notice: Subject to any disclaimer, the term of this patent is extended or adjusted under 35 U.S.C. 154(b) by 0 days.

(21) Appl. No.: 13/382,685

(22) PCT Filed: Jul. 7, 2010

(86) PCT No.: PCT/GB2010/001302
§ 371 (c)(1),
(2), (4) Date: Mar. 8, 2012

(87) PCT Pub. No.: WO2011/004153
PCT Pub. Date: Jan. 13, 2011

(65) Prior Publication Data
US 2012/0157772 A1 Jun. 21, 2012

(30) Foreign Application Priority Data
Jul. 8, 2009 (GB) .................................. 0911891.0

(51) Int. Cl.
*A61B 1/00* (2006.01)
*A61B 1/04* (2006.01)
*A61B 1/12* (2006.01)
*A61B 1/018* (2006.01)

(52) U.S. Cl.
CPC .............. *A61B 1/018* (2013.01); *A61B 1/0014* (2013.01); *A61B 1/00135* (2013.01)

(58) Field of Classification Search
USPC ....... 600/102, 104, 106, 107, 127–130, 153, 600/121–125, 156–159; 604/26, 43–45
See application file for complete search history.

(56) References Cited

U.S. PATENT DOCUMENTS

| | | | |
|---|---|---|---|
| 5,217,001 A | | 6/1993 | Nakao et al. |
| 5,259,366 A | * | 11/1993 | Reydel et al. ................ 600/124 |
| 5,400,768 A | * | 3/1995 | McNamara .... A61B 17/320016 600/104 |
| 5,483,951 A | | 1/1996 | Frassica et al. |
| 5,575,756 A | * | 11/1996 | Karasawa et al. ............ 600/157 |
| 2005/0234297 A1 | | 10/2005 | Devierre et al. |
| 2005/0267335 A1 | * | 12/2005 | Okada et al. .................. 600/173 |
| 2006/0258906 A1 | | 11/2006 | Binmoeller |
| 2007/0088247 A1 | * | 4/2007 | Bliweis ........................... 604/22 |
| 2008/0200765 A1 | * | 8/2008 | Mondschein ................. 600/157 |
| 2008/0277853 A1 | | 11/2008 | Menn |
| 2008/0281299 A1 | * | 11/2008 | Menn ................................ 606/1 |
| 2008/0319266 A1 | | 12/2008 | Poll et al. |
| 2009/0187069 A1 | * | 7/2009 | Terliuc ................. A61B 1/0055 600/106 |

FOREIGN PATENT DOCUMENTS

| | | | |
|---|---|---|---|
| CN | 1719997 A | 1/2006 | |
| DE | 10024728 A1 | * 11/2001 | ............... A61B 1/12 |

(Continued)

OTHER PUBLICATIONS

Application No. 201080030998, Office Action, 26 pages.

*Primary Examiner* — Ryan Henderson
(74) *Attorney, Agent, or Firm* — Price Heneveld LLP

(57) ABSTRACT

An accessory for partially enclosing a shaft of an endoscope is disclosed. The accessory defines a first space for accommodating the shaft and a second space for defining a conduit along the shaft. An outer surface of the accessory around the first and second spaces is centered on a first longitudinal axis, and the first space is centered on a second longitudinal axis spaced relative to the first longitudinal axis. The first space is open to one side, so that the accessory only partially encloses the shaft when placed around it.

15 Claims, 7 Drawing Sheets

(56) References Cited

FOREIGN PATENT DOCUMENTS

| | | |
|---|---|---|
| EP | 1607037 | 12/2005 |
| JP | 03-136630 | 6/1991 |
| JP | 06-189893 | 7/1994 |
| JP | 10-043131 | 2/1998 |
| JP | 2005-046273 | 2/2005 |
| JP | 2005046273 A * 2/2005 | ............... A61B 1/00 |
| JP | 2007-105314 | 4/2007 |
| JP | 2008-540041 | 11/2008 |

* cited by examiner

Figure 1 – Prior art

ACCESSORY CLIP FOR AN ENDOSCOPE

The present invention relates to an accessory for at least partially enclosing a shaft to define a conduit along the shaft. Particularly, but not exclusively, the shaft is of an optical device such as an endoscope.

Endoscopes are used in minimally invasive surgery (MIS) by surgeons to navigate and view inside a patient. There are a variety of sub-specialties of MIS and one such sub-speciality is Laparoscopy. Laparoscopy is MIS performed in the abdomen. The endoscope used in laparoscopy is called a laparoscope and is comprised of an elongate, typically cylindrical, shaft containing optical elements such as a camera, lighting provisions such as an optical fibre bundle and equipment. Laparoscopes are used for abdominal MIS to visualise the target anatomy in speciality areas such as laparoscopic general surgery, including upper and lower gastrointestinal and gynaecology and bariatrics as well as other surgical sectors utilising a rigid scope. In laparoscopy, the laparoscope is inserted through a cannula, which has been inserted through a small incision, just distal to the umbilicus (belly button) in the patient to access the abdominal cavity. The abdominal cavity is generally insufflated via this cannula, although other cannulae can be used, with carbon dioxide via an insufflator to create an operating space.

Endoscopes, for example laparoscopes, typically have a shaft housing optical equipment, for example lens and fibre optics or miniature cameras, for conveying an image in optical or electronic form from one end of the shaft to another end of the shaft where it can be viewed through an eyepiece or sent to a connector for connection to further equipment such as a video monitor. For the avoidance of doubt, the word "shaft" as used herein thus refers substantially to a longitudinally extending portion of the endoscope, irrespective of whether the endoscope is rigid or flexible.

During MIS, these other forms of access are created to access the area inside the body in which the operation is taking place. Through these further incisions in the patient, cannulae are inserted through which elongated instrumentation is delivered. However, it may be more desirable to access the operation site through a single cannula, to avoid causing further tissue trauma to the skin of the patient. Today in laparoscopic surgery there is an emphasis on reducing the number of access port positions required to effect the surgical procedure. For example, in laparoscopic cholesectomy a viewing port (at the umbilicus) is used for the laparoscope and a further three to four access or working ports are also introduced into the abdominal cavity. These working ports allow the surgeon to introduce those instruments necessary to manipulate organs and structures to effect the surgical procedure. Various companies are now introducing Single Incision Laparoscopic Surgery (SILS) or Single Port Access (SPA) approaches and associated instruments. This new surgical approach creates one transverse incision across the umbilicus that is of a size capable of accommodating multiple individual cannulae. The individual cannulae accommodate the optics and instruments to effect the surgical repair. In this way the patient only receives one abdominal incision as opposed to three or four in the example given above (Laparoscopic Cholesectomy).

One way of providing further access to the site of the operation through the same cannula as the laparoscope is to incorporate channels around the circumference of the laparoscope. These channels can be formed within a laparoscope sleeve. For example, United States Patent Application Publication US2008/0319266 A1 discloses a hollow, cylindrical tube adapted to surround a laparoscope. This tube has an outer wall which defines channels within it. The channels extend the length of the tube and are adapted to allow for the travel of gas and/or fluid along the length of the tube. The channels are radially relatively thin and are placed around the circumference of the laparoscope. The channels must be radially relatively thin so as to ensure that the diameter of the tube when the laparoscope is within it is small enough to fit through the cannula.

With reference to FIG. 1, an illustration of a prior art sleeve 2 for an endoscope is shown in cross-section. The sleeve 2 has an outer surface 4 and an inner surface 6. The outer surface 4 and inner surface 6 each define, in cross-section, a circle, and are both centred on a longitudinal axis 8, so that the circles are concentric. The circle defined by the outer surface 4 has a radius $a_1$ and the circle defined by the inner surface 6 has a radius $a_2$. The outer surface 4 and the inner surface 6 in combination define an annulus. The shaft (not shown) of the endoscope is accommodated within a shaft space 10, which is within the inner surface 6. When the shaft is within the shaft space 10, the inner surface 6 is in contact with the shaft. A number of channels 12 (in this example, five) are provided around the annulus between the inner surface 6 and the outer surface 4 of the sleeve 2. The channels 12 are of identical radial thickness.

SILS is driving down the number of abdominal incisions, however the size of the single incision imparts upon the number of individual cannula that it can accommodate. It has been found that there are situations in which it would be desirable to accommodate one or more channels of a relatively larger radial extent for a given outer diameter of the sleeve. For example, a channel of a larger radial extent could be used to pass a physical device, for example an MIS instrument, through the channel for use during surgery. However, providing a channel of larger radial extent tends to increase the overall diameter of the combined endoscope and sleeve, requiring larger incisions and cannulae, which is undesirable.

Aspects of the invention provide an accessory as defined in the appended independent claims. Additional optional features are set out in the dependent claims.

The accessory is of a simple construction and can be produced by a simple process such as injection moulding or extrusion. Thus, the accessory is inexpensive to produce, making it particularly suitable for being used as a disposable accessory.

The accessory is able to provide at least one conduit of a relatively larger radial extent than in the prior art for a given largest outer diameter of the accessory/laparoscope combination by positioning the laparoscope eccentrically within the accessory. This provides an area of larger radial extent at one side of the laparoscope between the exterior surface of the laparoscope and the adjacent outer surface of the accessory.

The eccentric arrangement of the laparoscope within the accessory allows for the accessory to be of a reduced diameter for a given conduit as compared to a central arrangement.

In some embodiments, the larger conduit allows for a physical device such as an MIS surgical instrument to be inserted through the conduit, which can be used during the procedure of an operation.

In some embodiments, the conduit is for transporting fluid to and/or from the distal end of a laparoscope.

In some embodiments, the accessory is operable to sealingly engage with the shaft to define the conduit.

In some embodiments, in cross-section, the outer surface of the accessory substantially defines at least part of a first circle.

In some embodiments, the accessory is substantially rigid.

In some embodiments, a plurality of conduits are provided, which may be used to provide access for a plurality of surgical instruments.

In some embodiments, the conduit has a more rounded cross-section than the thin channels of the prior art.

Embodiments of the invention are now described by way of example only, and with reference to the accompanying drawings in which.

Figure 1:
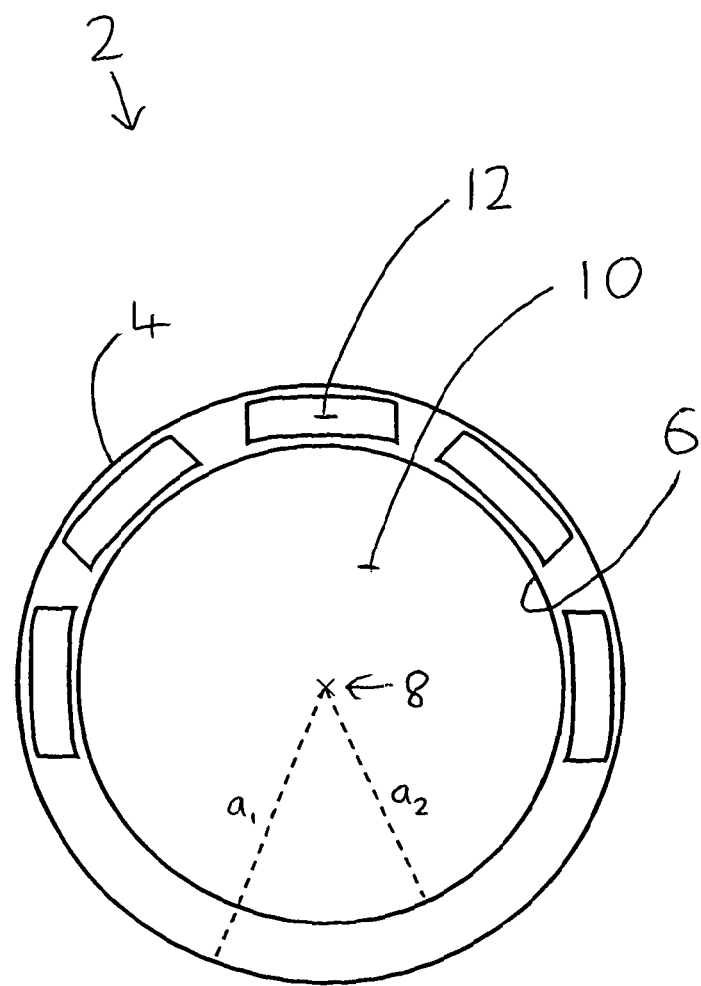
FIG. 1 depicts a cross-section of a prior art sleeve for an endoscope.
Figure 2:
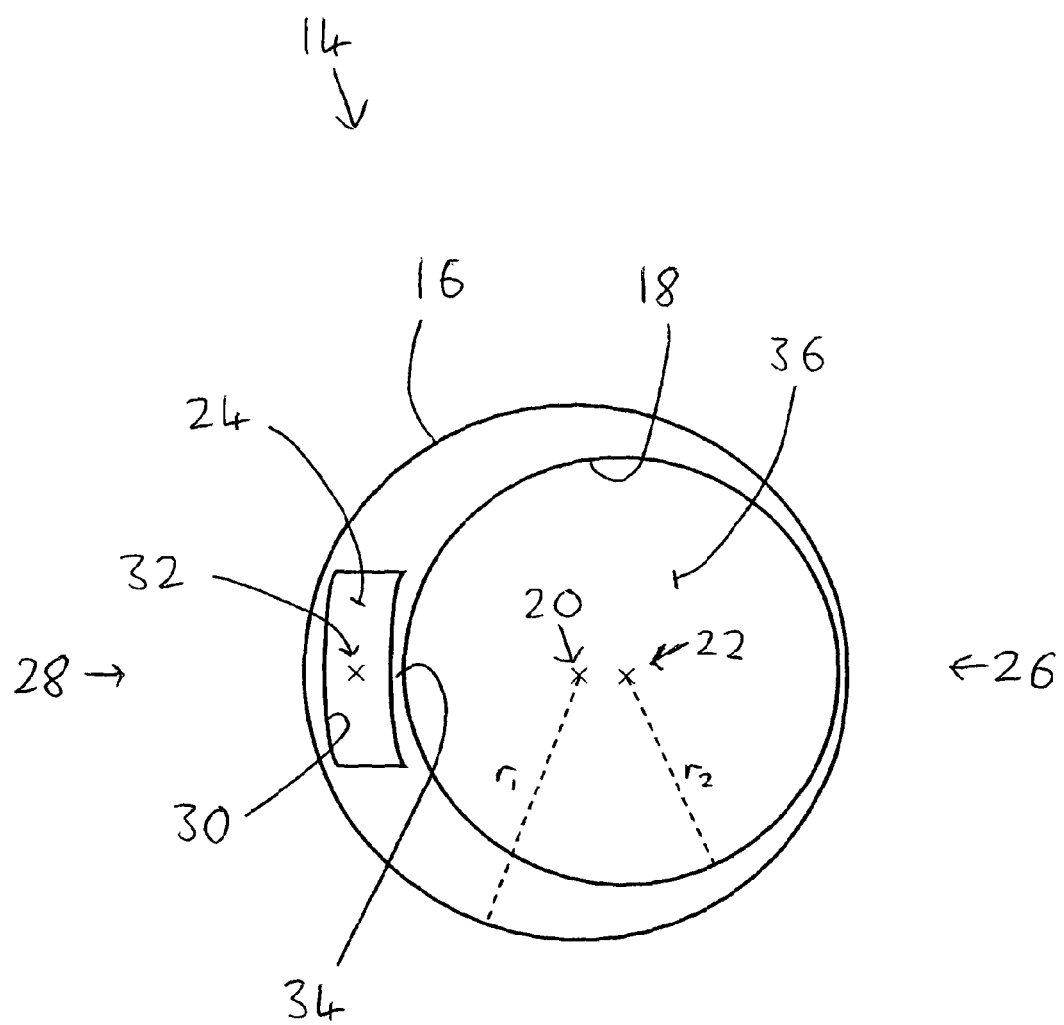
FIG. 2 depicts a cross-section of an accessory according to a first embodiment.

With reference to FIG. 2, a first embodiment of the invention is now described. An accessory 14 is shown in cross-section, with the accessory 14 extending longitudinally in a direction normal to the plane of the drawing. The cross-section of the accessory 14 is substantially the same across the length of the accessory 14, although in some embodiments it is structured differently at one or both of its ends, for example to provide fluid inlets or outlets. The accessory 14 comprises an outer surface 16 and an inner surface 18. The outer surface 16 is convex and the inner surface 18 is concave. The outer surface 16 is closed in on itself, as is the inner surface 18. Both the outer surface 16 and the inner surface 18 are substantially circular in cross-section and are centred on, respectively, a first longitudinal axis 20 and a second longitudinal axis 22, which are spaced relative to each other. The circle defined by the outer surface 16 has a radius $r_1$ and the circle defined by the inner surface 18 has a radius $r_2$, which is shorter in length than $r_1$. The inner surface 18 is fully contained within the outer surface 16. The centre of each of the circles lies on the respective longitudinal axis 20, 22. Thus, the centre of the circle defined by the inner surface 18 is offset from the centre of the circle defined by the outer surface 16.

The disclosed off-centre arrangement provides more space for accommodating a conduit 24 to one side 26 of the inner surface 18. As a consequence of this, the radial distance between the inner surface 18 and the outer surface 16 varies around the circumference of the outer surface 16. On one side 26 of the accessory 14, the outer surface 16 and the inner surface 18 are closest together. On an opposed side 28 of the accessory 14, the distance between the inner surface 18 and the outer surface 16 is at its maximum. In the region of the opposed side 28, the hollow conduit 24 is defined by the accessory 14. The conduit 24 extends between the outer surface 16 and the inner surface 18 of the accessory 14 and is defined by a conduit surface 30 centred on a third longitudinal axis 32. The three longitudinal axes 20, 22, 32 are substantially co-planar, so that the centre of a cross-section of the conduit 24 is substantially in line with the centres of the circles defined by the outer surface 16 and the inner surface 18. Between the conduit surface 30 and the adjacent part of the inner surface 18, a partition 34 is formed by the accessory 14. The accessory 14 is formed so that the conduit 24 is fully defined by the accessory 14. The partition 34 separates the conduit 24 from a shaft space 36 for accommodating the shaft (not shown) of a laparoscope. The shaft space 36 is defined by the inner surface 18 and is substantially disc-shaped in cross-section. Due to the relatively large size of the shaft space 36, i.e. that the diameter of circle defined by the inner surface 18 is more than half the diameter of the circle defined by the outer surface 16, the first longitudinal axis 20 passes through the shaft space 36.

In use, one end of the accessory 14 is held in position adjacent an end of the shaft of a laparoscope. The shaft is then inserted into the shaft space 36 along the second longitudinal axis 22 and the accessory 14 is slid along the shaft so that the shaft is substantially contained within the accessory 14. The accessory 14 containing the shaft is able to pass through a cannula, which has been inserted through a small incision in a patient to access, for example, the abdominal cavity.

Figure 3:
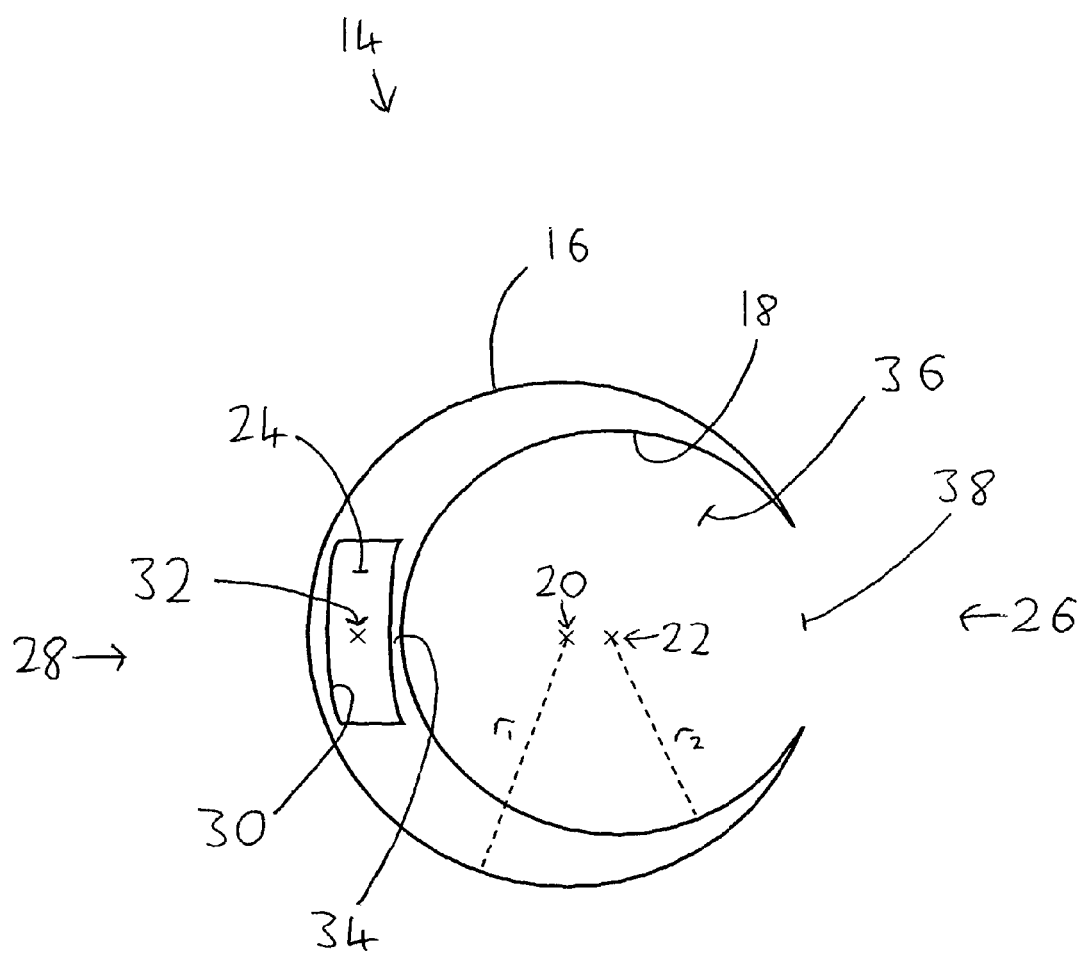
FIG. 3 depicts a cross-section of an accessory according to a second embodiment.

With reference to FIG. 3, an accessory 14 according to a second embodiment of the invention is now described. The accessory 14 of the second embodiment is similar to the accessory 14 of the first embodiment. The main difference between the first and second embodiments is that the outer surface 16 and the inner surface 18 are not fully circular in cross-section. Instead, the outer surface 16 and the inner surface 18 are connected, and form a generally crescent-shaped cross-section with an opening 38 on one side 26, i.e. on one longitudinal side of the accessory 14. The opening extends along the entire length of the accessory. The opening 38 is opposite the conduit 24.

In use, when the shaft is within the shaft space 36, part of the exterior surface of the shaft is exposed through the opening 38. In some embodiments, the accessory 14 is arranged to be slid on to the shaft in the same way as described for the first embodiment. In some embodiments, the accessory 14 is flexible such that the opening 38 can be widened and the shaft placed directly into the shaft space 36. The accessory 14 then closes around the shaft due to an elastic force and holds the shaft in place.

Figure 4:
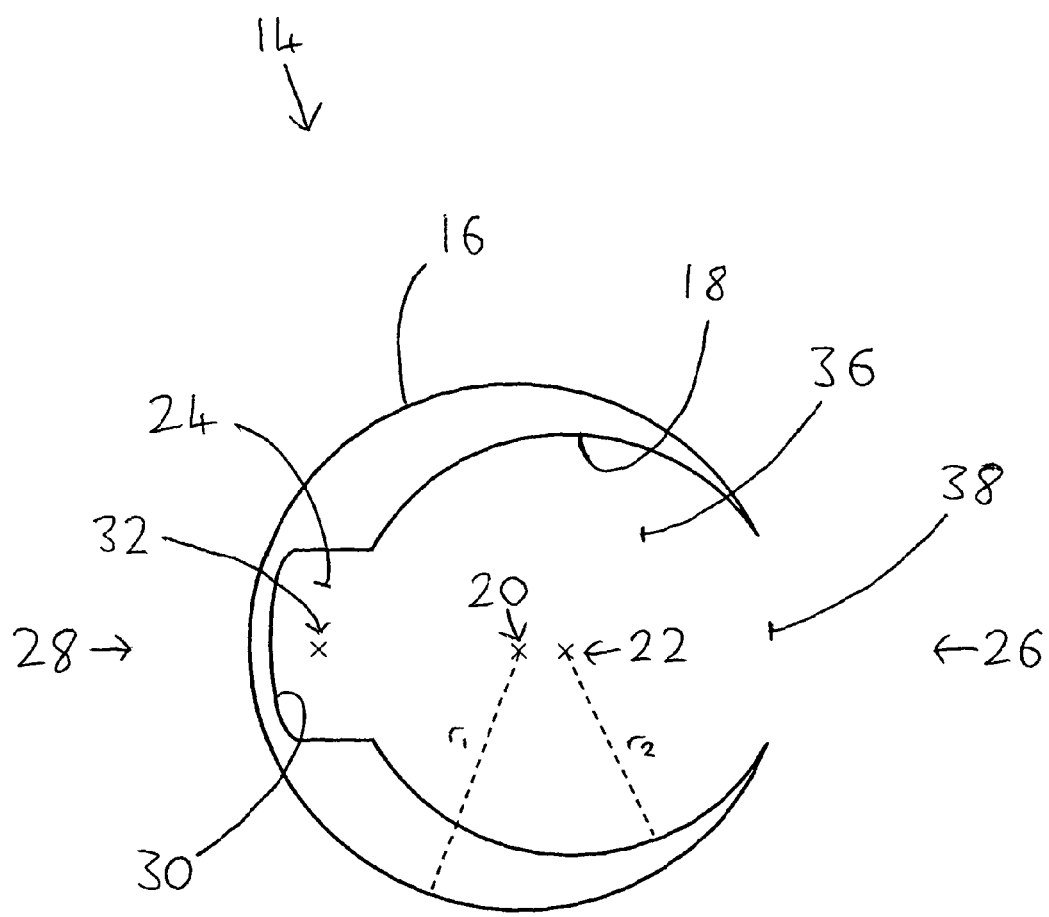
FIG. 4 depicts a cross-section of an accessory according to a third embodiment.

With reference to FIG. 4, an accessory 14 according to a third embodiment of the invention is now described. The accessory 14 of the third embodiment is similar to the accessory 14 of the second embodiment. The main difference between the accessory 14 of the second embodiment and the accessory 14 of the third embodiment is that the accessory 14 of the third embodiment has no partition 34 between the shaft space 36 and the conduit 24. Therefore, the inner surface 18 and the conduit surface 30, and the spaces they define, are connected. The conduit 24 is only fully defined when the shaft of a laparoscope is situated within the shaft space 36. When the shaft is in position, the conduit surface 30 combines with part of the external surface of the shaft to define the conduit 24. In some embodiments, the conduit surface 30 combines with part of the exterior surface of the shaft to form a sealed conduit 24 for transporting fluids.

Figure 5:
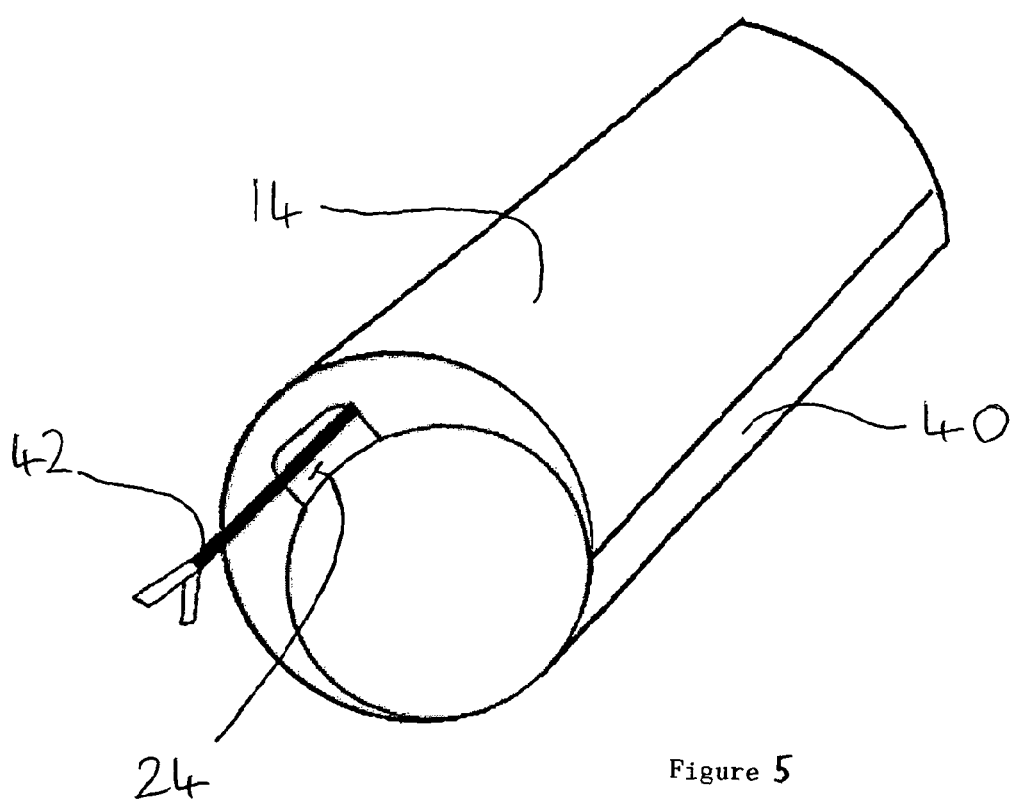
FIG. 5 depicts an accessory according to the third embodiment in use with a laparoscope and a medical instrument.

With reference to FIG. 5, an example of the use of the accessory 14 of the third embodiment is described. The accessory 14 is in place around a laparoscope 40. A medical instrument 42, such as a grasper, biopsy forcep, or snare extends through the conduit 24. In some embodiments, a second conduit is defined within the laparoscope 40 (or other shaft) for providing access for instrumentation.

Figure 6:
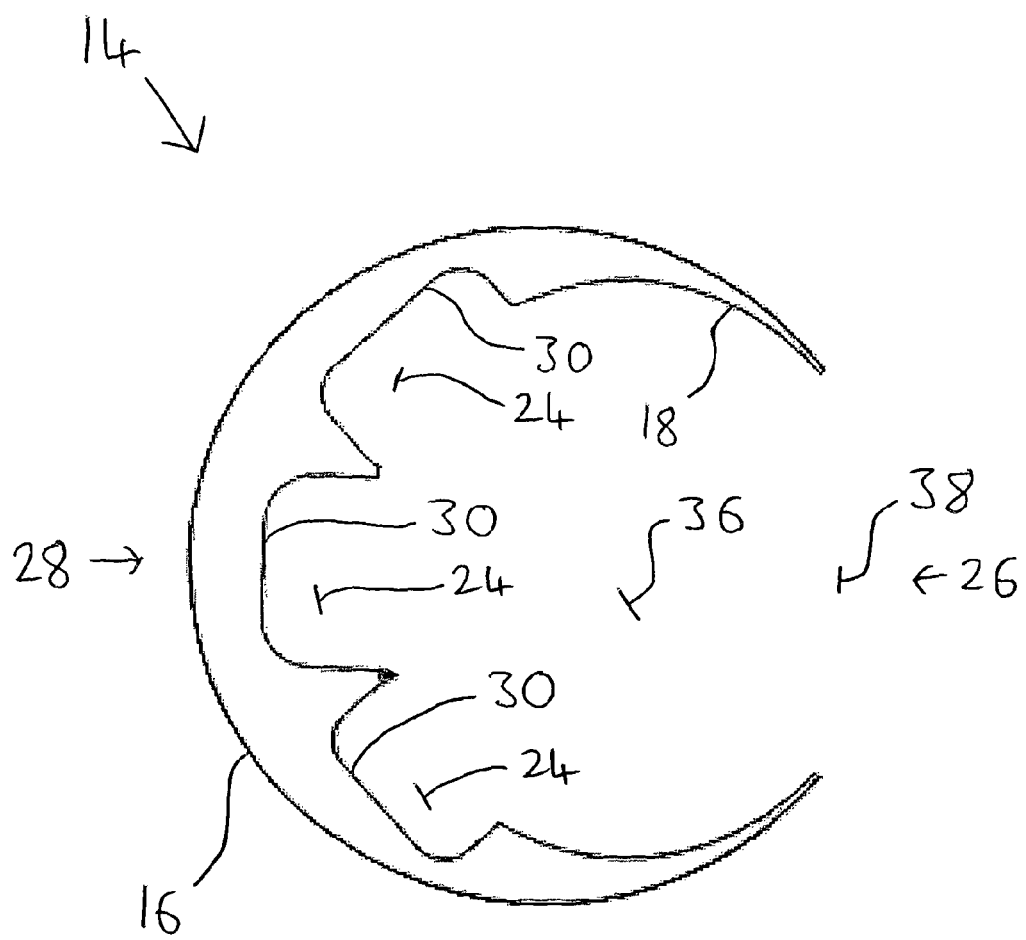
FIG. 6 depicts an accessory, similar to that of the third embodiment, which defines three conduits.

With reference to FIG. 6, an accessory 14 similar to that of the third embodiment is described. The accessory 14 defines three conduits 24, with one on either side of the conduit 24 of the third embodiment. The conduits 24 are all proximal to the opposed side 28.

Figure 7:
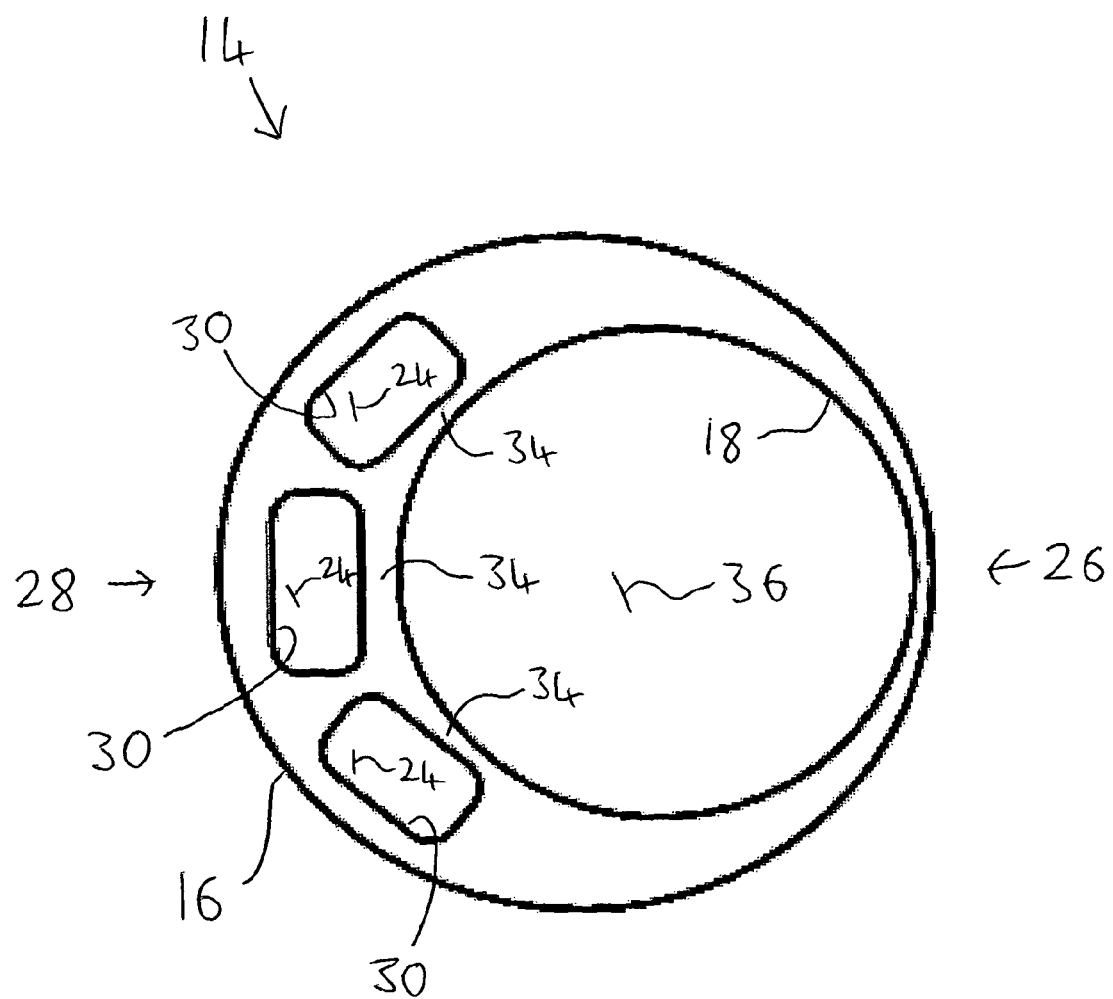
FIG. 7 depicts an accessory, similar to that of the first embodiment, which defines three conduits.

With reference to FIG. 7, an accessory 14 similar to that of the first embodiment is described. The accessory 14 defines three conduits 24, with one on either side of the conduit 24 of the first embodiment. The conduits 24 are all proximal to the opposed side 28. Equally, embodiments providing a plurality of conduits based on the second embodiment are also disclosed.

It will be understood that the above description of specific embodiments of the invention is by way of example only and it is not intended to limit the scope of the invention. Many modifications and alterations of the specific embodiments described above will be apparent to a person skilled in the art and are intended to be within the scope of the appended claims.

In some embodiments, the accessory 14 is substantially rigid, for example, for use with a laparoscope. The rigid accessory 14 keeps its shape and form so that it always defines the conduit 24 and the shaft space 36, irrespective of the presence of the shaft in the shaft space 36.

In some embodiments, the accessory 14 is flexible, for example, for use with a flexible endoscope or any other device having a flexible shaft.

In some embodiments, the accessory 14 holds the shaft in place due to an elastic force on the shaft when the shaft is in the accessory 14.

In some embodiments having the opening 38, the tips defined by the points at which the outer surface 16 and the inner surface 18 meet are bent inwards such that they grip the shaft when the shaft is in the accessory 14.

In some embodiments, the outer surface 16 of the accessory 14 defines, in cross-section, a circle, square, triangle, ellipse, oval or any other shape. In some embodiments, the shape defined by the inner surface 18 of the accessory 14 in cross-section corresponds with the shape defined by the exterior surface of the shaft in cross-section. In particular, in some embodiments, the cross-sectional shape is elongated with the longitudinal axes 20, 22, 32 spaced along the elongated direction. These embodiments may minimise the accessory 14 material used for certain configurations of the shaft space 36 and conduit 24.

In some embodiments, the conduit 24 defines, in cross-section, a circle, square, triangle, ellipse, oval or any other shape. In particular, the conduit 24 substantially fills a space between the outer surface 16 adjacent the opposed side 28 of the accessory 14 and the inner surface 18.

In some embodiments, a plurality of conduits 24 are formed by the accessory 14, or by the accessory 14 and the shaft in combination. In some embodiments, the conduits are proximal to the opposed side 28.

In some embodiments, the accessory 14 has an elongate transverse cross-section. In some embodiments, the outer surface 16 and the inner surface 18 define different shapes in cross-section. For example, in some embodiments, the inner surface 18 of the accessory 14 defines a circle in cross-section, and the outer surface 16 of the accessory 14 defines an oval in cross-section.

In some embodiments, the outer surface 16 of the accessory 14, however shaped, is centred on a first longitudinal axis 20 and the shaft space 36 is centred on a second longitudinal axis 22, which is spaced apart from the first longitudinal axis 20. In some embodiments, the conduit 24 is centred on a third longitudinal axis 32 which is co-planar with the first and second longitudinal axes 20, 22 and, specifically, the resulting plane is aligned with a transverse direction of elongation in some embodiments in which the accessory 14 has an elongate transverse cross-section.

In some embodiments, the shaft is removably insertable into the first space.

In some embodiments, the accessory 14 is formed integrally with the laparoscope, such that the endoscope is accommodated in the first space.

Further embodiments combine any one or more features of the described embodiments with each other, to the extent that they are not mutually exclusive.

Although some of the above embodiments have been described with respect to a laparoscope, in some embodiments, the accessory 14 is used with other types of endoscope, such as a borescope or a fibrescope or any like device which may be used for medical or non-medical applications. The accessory 14 may be useable with any suitable elongate, generally cylindrical shaft, for example of a CCTV or other type of film, video or still camera, or of or for a microscope or telescope.

The invention claimed is:

1. An accessory for partially enclosing a shaft of an endoscope, the accessory comprising:
a first end, a second end and, a longitudinal portion extending longitudinally between the first and second ends, a cross-section of the accessory at the second end being structured differently from a cross-section of the accessory at the longitudinal portion to provide a fluid outlet, the longitudinal portion of the accessory defining a first space for accommodating the shaft of the endoscope and a second space for defining a conduit along the shaft for transporting fluid to a distal end of the endoscope, wherein, in a transverse cross-section of the longitudinal portion, the first space has a generally circular shape, and the second space has a generally rectangular shape with at least one curved side; wherein the accessory is configured to hold the shaft in place due to an elastic force on the shaft when the shaft is in the accessory;
an outer surface around the first and second spaces, wherein the outer surface is centered on a first longitudinal axis, and the first space is centered on a second longitudinal axis spaced relative to the first longitudinal axis, the first space being open to one side, so that the accessory only partially encloses the shaft when placed around it; and
an inner surface, wherein the inner surface is within the outer surface,
wherein a wall is formed by the inner and outer surfaces, and wherein the wall continually increases in thickness from the tips to the second space;
wherein the outer surface and the inner surface of the accessory form a generally crescent-shaped cross-section having tips at the open side which are bent inward and grip the shaft when the shaft is in the accessory, such that the accessory is widened and closes around the shaft to exert an elastic force on the shaft and grip the shaft in place, and
wherein the first and second spaces are adjoining so that the accessory is operable to co-operate with the shaft to define the conduit.

2. The accessory of claim 1, wherein the accessory is operable to sealingly engage with the shaft to define the conduit.

3. The accessory of claim 1, wherein, in cross-section, the second space is closer to the first longitudinal axis than it is to the second longitudinal axis.

4. The accessory of claim 1, wherein the second space is centered on a third longitudinal axis, and the first, second and third longitudinal axes are substantially coplanar.

5. The accessory of claim 1, wherein, in cross-section, the outer surface of the accessory substantially defines part of a first circle having a center, the center of the first circle being located on the first longitudinal axis.

6. The accessory of claim 1, wherein, in cross-section, an inner surface of the accessory substantially defines part of a second circle having a center, the center of the second circle being located on the second longitudinal axis.

7. The accessory of claim 1, in which the accessory has an elongate transverse cross-section.

8. The accessory of claim 1, wherein the endoscope is a laparoscope.

9. The accessory of claim 1, wherein the second space is one of a plurality of spaces for defining a plurality of conduits along the shaft.

10. The accessory of claim 1, wherein the accessory is substantially rigid.

11. The accessory of claim 1, wherein the first longitudinal axis passes through the first space.

12. The accessory of claim 1, wherein the shaft is removably insertable into the first space.

13. The accessory of claim 1, wherein the endoscope is accommodated in the first space.

14. The accessory of claim 13, wherein a second conduit for providing access for instrumentation is defined within the endoscope.

15. A surgical device, comprising:
an endoscope; and
the accessory of claim 1, the accessory being formed integrally with the endoscope;
wherein the endoscope is accommodated in the first space, and wherein a second conduit for providing access for instrumentation is defined within the endoscope.

* * * * *